Figure 1:
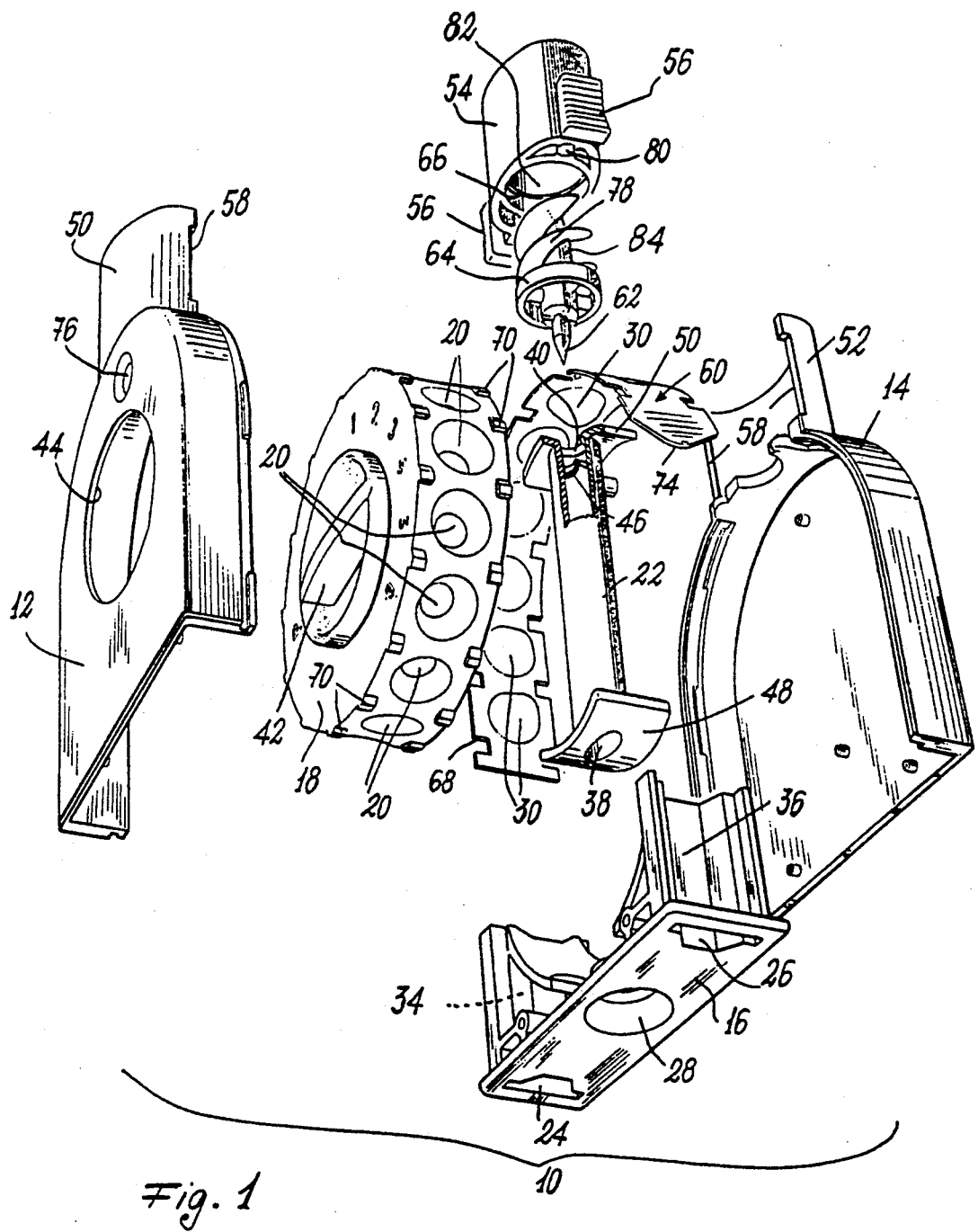

United States Patent [19]

Cocozza et al.

[11] Patent Number: 5,207,217
[45] Date of Patent: May 4, 1993

[54] MULTIPLE SINGLE-DOSE INHALER FOR MEDICAMENTS IN POWDER FORM

[75] Inventors: Salvatore Cocozza, Milan; Gianfranco Citterio; Maurizio Rusconi, both of Merate, all of Italy

[73] Assignee: Promo Pack SA, Switzerland

[21] Appl. No.: 722,873

[22] Filed: Jun. 28, 1991

[30] Foreign Application Priority Data

Jul. 16, 1990 [IT]  Italy .............................. 20947 A/90

[51] Int. Cl.[5] .......................................... A61M 15/00
[52] U.S. Cl. ............................. 128/203.21; 128/203.15
[58] Field of Search .................... 128/203.12, 203.15, 128/203.21

[56] References Cited

U.S. PATENT DOCUMENTS

| | | | |
|---|---|---|---|
| 3,795,244 | 3/1974 | Lax et al. | 128/203.15 |
| 3,807,400 | 4/1974 | Cocozza | 128/203.15 |
| 3,870,046 | 3/1975 | Elliott | 128/203.15 |
| 4,627,432 | 12/1986 | Newell et al. | 128/203.21 |
| 4,811,731 | 3/1989 | Newell et al. | 128/203.15 |
| 4,860,740 | 8/1989 | Kirk et al. | 128/203.15 |

FOREIGN PATENT DOCUMENTS 0129985 1/1985 European Pat. Off. .
2516387 5/1983 France .

Primary Examiner—Edgar S. Burr
Assistant Examiner—Aaron J. Lewis
Attorney, Agent, or Firm—Steinberg & Raskin

[57] ABSTRACT

An inhaler (10) of the multiple single-dose type for administering doses of medicament in very fine or micronized powder form contained in blisters (30) in a blister sheet (60) comprises means (18) for bringing the blisters (30) of the blister sheet one after another into a piercing position, means (62) for piercing the individual blister, a delivery channel through which the patient exerts the inhalation action, and an air intake which communicates with the delivery channel (82) when a blister has been pierced. The blister sheet (60) is in the form of a strip with the blisters (30) aligned. A connection channel (22) is provided to connect the delivery channel (82) to the air intake (28). The blister (30) when in its piercing position is interposed between the delivery channel (82) and the connection channel (22). In this latter there is provided a cup (46) coaxial with the connection channel (22) and with its concavity facing the blister in the piercing position.

9 Claims, 2 Drawing Sheets

MULTIPLE SINGLE-DOSE INHALER FOR MEDICAMENTS IN POWDER FORM

This invention relates to inhalers, i.e. devices for administering medicaments in very fine or micronized powder form.

The administration is achieved by the patient inhaling through an appropriate mouthpiece provided on the inhaler, and which is applied to the mouth.

One type of known single-dose inhaler delivers a dose of medicament in powder form contained in a capsule, which is inserted into the inhaler and then perforated or otherwise opened. An air stream, generated by the sucking action of the patient, removes the powdered medicament from the open capsule to administer it to the patient.

Instead of the said mouthpiece, the inhaler can comprise a suitable nasal adaptor to enable the patient to inhale through a single nostril.

Some examples of single-dose inhalers are described in U.S. Pat. Nos. 3,807,400, 3,991,761, 3,906,950 and 4,013,075.

EP-A-0,211,595 describes a type of multiple single-dose inhaler, which receives a circular blister sheet comprising radial blister, each containing a dose of medicament in powder form. The inhaler is provided with means for bringing one blister after another into a piercing position, and means for piercing the blister. When the piercing means are operated the medicament dose contained in the blister falls into a chamber below the piercing position. The chamber is traversed by an air stream generated by the sucking action of the patient. The powder medicament is thus dispersed into the air stream and is inhaled by the patient. The multiple single-dose inhaler has however certain drawbacks. In particular, because of their shape, circular blister sheets have a certain bulk which governs the dimensions of the pack in which they are sold.

In addition the air stream generated by the suction action of the patient travels substantially at a right angle. In this respect, the air is drawn through the hole produced in the blister as a consequence of its piercing. The axis of this hole is substantially vertical and lies above said chamber which is to receive the dose of powder medicament falling from the pierced blister. The aperture through which the air stream leaves the chamber, which communicates with the mouthpiece, is coaxial to this latter, the relative axis extending horizontally. The air stream therefore deviates at said chamber, which is fairly large. Thus in the chamber there are regions which are incompletely or only marginally swept by the air stream generated by the inhalation. It can therefore happen that the dose of medicament present in the chamber is not entirely removed. This occurs particularly if the patient, having operated the blister piercing means, does not maintain the inhaler rigorously horizontal when he holds it to his mouth, so that the dose of medicament is able to move into marginal regions of the chamber, Again, the said chamber is in fact formed of two parts, a lower part integral with the mouthpiece and an upper part delimited laterally by walls integral with the rotatable circular support which carries the blister sheet and forms part of said means for bringing the individual blisters into the piercing position. A slit is present between the two said chamber parts at about half the chamber height.

It often happens that in bringing the inhaler to the mouth, the patient does not maintain the inhaler rigorously horizontal as he should, but accidentally inclines it to the horizontal by an angle which may even approach 90°. Consequently, instead of lying on the base of the chamber, the dose of powdered medicament lies on its side wall, this wall comprising said slit. For constructional reasons this latter cannot in all cases be so small as to prevent the powdered medicament, the granules of which can have a size of the order of microns, from partly falling out of the chamber through the slit.

There is then the rather serious drawback that the dose effectively inhaled by the patient is less than that prescribed. In addition that part of the medicament which escapes through said slit disperses to soil the interior of the inhaler.

This is confirmed by the fact that the cited patent application states that the inhaler is provided with a brush for cleaning the inhaler. In reality, after the inhaler has been used for a certain period, on opening it can be seen that its interior is covered with the powder of the medicament, which can be removed by the said brush. This brush is also used to remove any powder which accumulates in the corners of said chamber.

The present invention proposes to obviate the aforesaid drawbacks of the multiple single-dose inhaler of the known art, in particular by providing an inhaler which besides being simple and comfortable to use, utilizes a blister sheet of minimum overall size.

Said object is attained by the inhaler of the present invention, comprising means for bringing the blisters of a blister sheet one after another into a piercing position, means for piercing the individual blister when in the piercing position, a delivery channel through which the patient exerts the inhalation action, and an air intake which communicates with said delivery channel when a blister has been pierced, the released dose of medicament being removable by the air stream generated by the inhalation, characterized in that the blister sheet is in the form of a strip with the blisters aligned, there being provided a channel of rectilinear axis, coaxial with the delivery channel and connecting this latter to the air intake, the individual blister when in its piercing position being interposed between the delivery channel and the connection channel, within the connection channel in proximity to that end thereof adjacent to the blister when in its piercing position there being provided a cup coaxial with the connection channel, the concavity of the cup facing said blister, the cup having smaller dimensions than the dimensions of the connection channel at the position occupied by the cup.

During piercing of the blister the inhaler must be held with the delivery channel substantially vertical so that the dose of medicament in powder form contained in the blister falls into said cup on piercing, the dimensions of which are such that the powder falls into it even if the inhaler is not rigorously maintained with the connection channel (and hence the delivery channel, i.e. the mouthpiece or nasal adaptor) vertical.

By providing the cup with a suitable concavity and making the cup of convenient capacity and preferably a capacity substantially greater than the volume of the medicament dose, in bringing the inhaler to the mouth or nostril after piercing a blister it is not necessary to maintain the mouthpiece or nasal adaptor rigorously vertical.

In this respect, by choosing a suitable diameter and a suitable cup concavity, even if the delivery channel is inclined significantly to the vertical, which can inadvertently happen while the patient brings the inhaler to his mouth, it is difficult for the medicament dose to fall out of the cup.

Only by inclining the inhaler at large angles to the vertical (approaching 90°) can the powdered medicament fall out of the cup, but it then rests against the inner wall of said connection channel. The inclination at which the powder falls out of the cup is even greater than might be expected because the powder has a certain resistance to flow. For this latter reason and the fact that when the powder falls from the cup the inclination of the connection channel to the horizontal is only slight, the powder is unable to fall out of said channel and can therefore be all used on inhalation.

From the aforegoing it is apparent that the inhaler according to the invention does not need to be provided with a brush as it does not require cleaning.

The use of blister strips instead of the circular blister sheets of the known multiple single-dose inhaler results in a considerable reduction in the size of the blister pack.

In one embodiment of the multiple single-dose inhaler according to the invention the means for bringing the blisters in succession into their piercing position consist of a hollow drum rotatable about its axis to carry the blisters, one after another, into the piercing position, the lateral surface of the drum having equidistant seats communicating with the drum interior and arranged to receive the blisters of the blister strip, this latter when inserted into the inhaler being wrapped at least through a certain portion about said drum, the connection channel being disposed within the drum, that end of said channel towards which the concavity of the cup faces being in a position corresponding with the piercing position.

Conveniently, the blister piercing means consist of a plunger or point disposed coaxially within the delivery channel and axially movable in both directions.

According to one embodiment of the present invention the piercing plunger or point is rigid with the delivery channel, this latter being axially movable in both directions to pierce the blister lying in the piercing position.

To improve the dispersion of the medicament dose into the air stream generated by the inhalation of the patient, a vortex generating means is provided in the delivery channel.

Preferably, this means consists of a fixed coaxial helix carried by a coaxial shaft. Compared with laterally supported helixes with a free axial channel, this helix with its coaxial support shaft prevents the turbulence created by the patient following inhalation from concentrating the medicament powder within the central part of the flow. This results in a more uniform distribution of the medicament particles throughout the entire cross-section of the air stream leaving the delivery channel. Preferably the blister strip comprises in one or both edges a series of equidistant notches to be engaged by corresponding drive teeth provided on said drum. Simple drive means are hence obtained for bringing the individual blisters, one after another, into the piercing position following rotation of the drum. Alternatively, instead of the initial blister inserted into the inhaler, a false blister projecting to a lesser extent than the other blisters can be provided. This false blister, by engaging one of the blister seats provided in the drum, allows the blister strip to be dragged by the drum when rotated.

To obtain more regular and precise advancement of the blister strip, the drum can be provided both with said notches and with the false blister.

Figures 2, 3:
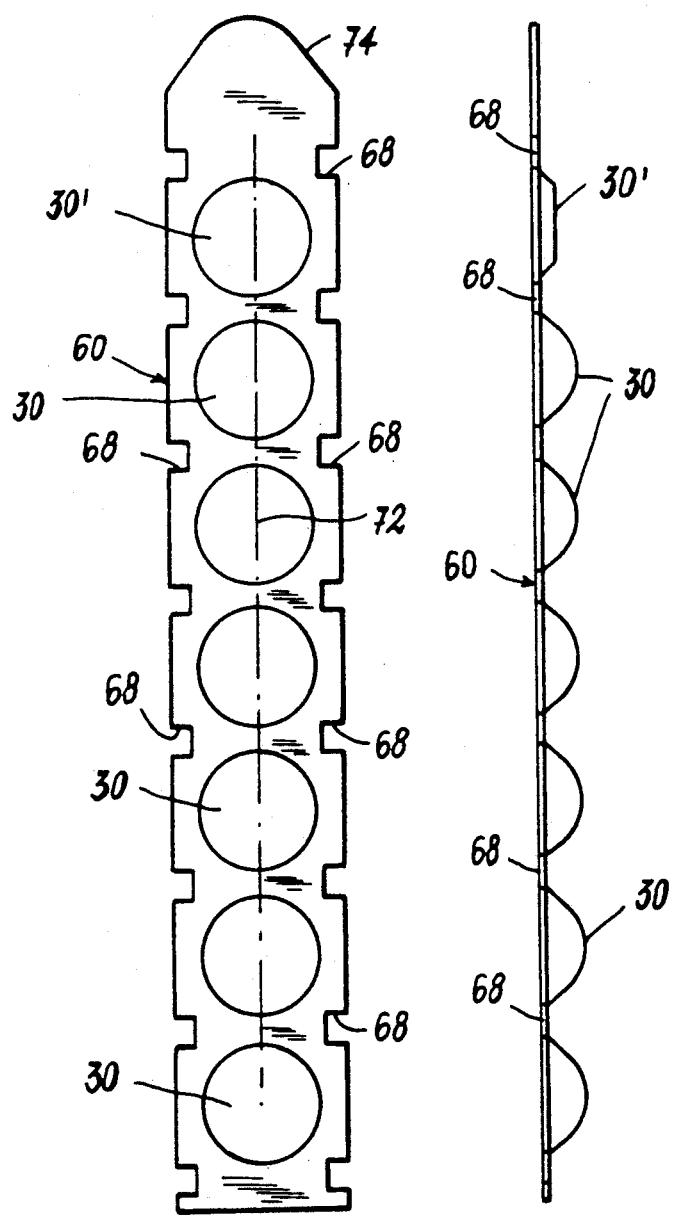

The invention will be more apparent from the description of one embodiment given hereinafter by way of example only. In this description, reference is made to the accompanying drawings, in which:

FIG. 1 is an exploded perspective view of the inhaler;
FIG. 2 is a plan view of a blister strip; and
FIG. 3 is a view thereof in profile.

From FIG. 1 it can be seen that the inhaler 10 comprises an outer casing formed from a left half-casing 12 and a right half-casing 14, which are substantially equal, and a closure element or base 16.

The two half-casings 12 and 14 enclose a drum 18 supported rotatable about its horizontal axis by the half-casings. The drum 18 is internally hollow and is open at one end, namely at its right hand end. It comprises in its lateral surface a series of equidistant apertures or seats 20 for receiving the blisters 30 of a blister strip 60, which can be partially wrapped about the drum 18 in the manner explained hereinafter.

Within the right half-casing 14 there is fixed a tubular element or connection channel 22 in a vertical diametrical position within the drum 18.

In the base 16 there is an aperture or air intake 28 coaxial with the connection channel 22 and communicating with it when a seat 20 of the drum 18 corresponds with said air intake 28.

The base 16 comprises two slots 24 and 26 associated with respective guides 34, 36 for the blister strip 60. The blister strip 60 is inserted into the inhaler 10 through the first slot 24 and can be extracted through the second slot 26 when all its blisters 30 have been used.

The rotatable drum 18 represents a drive mechanism which enables one blister after another to be brought into a position, i.e. the piercing position, in which two diametrically opposing seats 20 of the drum 18 correspond with the open ends 38 and 40 of the connection channel 22, the blister to be pierced being contained in that of the two said seats which corresponds with the aperture 40.

To facilitate the operation of arranging a blister 30 of the blister strip 60 in said piercing position, a mechanism can be provided to rotate the drum 18 stepwise, a blister being moved into the piercing position at each step. The drum 18 is rotated via a knob or gripping fin 42 provided on the left end 44 (FIG. 1) of the drum 18 and fixed to this latter. The knob 42 projects outwards through a circular hole 44 provided in the left half-casing 12.

Within the connection channel 22 in proximity to its aperture 40 there is provided a circular cup 46 coaxial with the channel 22 and of smaller diameter than the inner diameter of said channel 22. The cup 46 has its concavity facing the aperture 40 and is retained in position by three spokes fixed 120° apart to the internal wall of the connection channel 22. To the side of the cup 46 there is sufficient free space to allow an air stream of the required flow to pass.

As can be seen in FIG. 1, the ends of the connection channel 22 are shaped as a curved flange, 48 and 50 respectively, in order to match the shape of the internal cylindrical wall of the drum 18. Each of the two half-casings 12 and 14 comprises an upper protuberance 50 and 52 respectively. When the inhaler is assembled, the two parts 50 and 52 enclose the mouthpiece 54, which is placed to the mouth of the patient. The mouthpiece 54 encloses a delivery channel 82.

In the illustrated embodiment of the inhaler according to the present invention, the mouthpiece 54 can be moved vertically in both directions. To achieve this, the mouthpiece 54 comprises two opposing knurled grips 56 projecting outwards through relative apertures 58 provided in the parts 50 and 52 which surround the mouthpiece 54.

The mouthpiece 54 is retained in its most outer position by the action of a pair of springs (not shown) inserted into symmetrical cavities (of which only one can be seen in FIG. 1).

Coaxially with and in the interior of the mouthpiece 54 there is provided a coaxial point 62 for piercing the blisters 30 of the blister strip 60. The point 62 is kept centered within the mouthpiece by a ring 64 fixed to it. The ring 64 can be forced beyond the step 66 provided within the mouthpiece 54, to fix it to the mouthpiece. Consequently, when the mouthpiece is pushed downwards using the grips 56, the point 62 also moves downwards. If a blister 30 of the blister strip 60 is in the piercing position, the point pierces the blister. On releasing the mouthpiece 54, it returns under the action of said return springs to its most outer position. The dose of medicament contained in the pierced blister consequently falls into the underlying cup 46 which, as stated, has a capacity substantially greater than the volume of the medicament dose which falls into it. Because of this and because of the convenient concave shape of the cup 46, even if the patient does not maintain the inhaler rigorously vertical in placing it to his mouth, the medicament cannot escape from the cup. This does not happen even for large angles of inclination to the vertical.

Even if the patient in bringing the inhaler to his mouth should incline it by such an angle that the medicament falls out of the cup 46, the inclination of the connection channel 22 to the vertical would have to be very large because of the large cup concavity. This means that the inclination of said connection channel 22 to the horizontal would be only small and hence as the medicament powder has a certain resistance to flow, the powder which falls into the connection channel 22 would be unable to escape from said channel (and hence would not be lost as it can be still inhaled by the patient).

The blister strip 60 already mentioned with reference to FIG. 1 is shown to an enlarged scale in FIGS. 2 and 3. It is in the form of a strip with a somewhat pointed end 74 to facilitate its insertion through the slot 42 of the inhaler 10. Both edges of the blister strip 60 comprise a series of equidistant notches 68 to engage to corresponding series of teeth 70 provided on the drum 18 of the inhaler 10.

As stated, the blister strip 60 comprises a series of blisters 30 centered about the strip axis 72. As is well known, a blister strip is formed of two foils of mutually bondable material. One of the two foils can be of transparent material while the other is normally opaque and generally of aluminium. In the specific described case both the foils are of aluminium. One of the two foils is shaped to form pockets in it of overall frusto-conical shape with a rounded tip, whereas the other foil is flat and is bonded onto the other after the pockets of this latter foil have been filled with the dose of medicament in powder form, to thus seal the pockets.

The piercing point 62 must be able to pierce both said foils without requiring excessive force by the patient.

Preferably that blister 30' closest to the tip 74 of the blister strip 60 projects to a lesser extent than the other blisters and does not contain medicament, its only purpose being to facilitate insertion of the strip into the inhaler. It is therefore a false blister and facilitates the engagement of the strip 60 with the drum 18 when the strip is inserted into the inhaler.

Alternatively an inhaler can be formed in which the mouthpiece 54 is fixed and only the piercing point 62 is mobile in each direction.

The operation of the described inhaler is apparent to an expert of the art. However this operation will be described briefly for clarity.

When the drum 18 has been rotated into a predetermined loading position to be known as the position P, the tip 74 of the blister strip 60 is inserted through the relative slot 24 in the inhaler as far as possible. It is then only necessary to rotate the inhaler knob 42 with one hand for the false blister 30' to enter one of the seats 20 of the drum 18. Simultaneously the two series of teeth 70 on the drum 18 engage the relative notches 68 of the strip 60 to ensure reliable and precise advancement of the blister strip when the knob 42 is rotated. On that face of the drum which carries the knob 42 there is provided progressive numbering corresponding to the number of blisters 30, in this specific case from 1 to 6. These numbers are visible through a window 76 provided in the left half-casing 12 of the inhaler. Through the window 76 there is visible a letter P which defines said loading position. Hence when the tip 74 of the blister strip 60 has been inserted with the drum in the position P and the drum rotated clockwise until the number 1 appears in the window 76, the inhaler is ready for piercing the first blister. Maintaining the inhaler vertical as in FIG. 1, it is necessary only to press the mouthpiece 54 downwards as far as possible using the grips 56 to cause the point 62 to pierce both constituent foils of the blister strip 60. On releasing the grip the mouthpiece 54 returns to its most projecting position by the action of said return springs (not shown), and pulls with it the point 62. Consequently the dose of medicament in powder form contained in the pierced blister 30 falls into the cup 46. This latter has a volume substantially greater than the dose of medicament and has a diameter substantially greater than that of the hole produced in the blister strip by the point 62. Because of this, the dose of powder falls into the cup 46 even if the inhaler is not maintained perfectly vertical.

At this point the patient has only to put the inhaler mouthpiece 54 to his mouth and inhale. The air stream produced within the connection channel 22 encounters the cup, passes by it and generates downstream of it a vortex which removes the entire dose of medicament powder contained in it by entrainment by the air stream.

The presence of the helix 78 within the mouthpiece 54 improves mixing of the powder with the air before it reaches the patient's mouth. The helix is carried by a shaft 84 coaxial with the piercing point 62.

If the drum 18 is now moved into the position indicated by the number 2 visible through the window 76, the inhaler is ready for its second delivery, and so on until the last position, 6, corresponding to the last available blister 30.

When in this latter position the tip 74 of the blister strip 60 projects from the exit slot 26, hence by rotating the drum 18 clockwise by the knob 42 the empty blister strip can be extracted from the inhaler, which is hence ready for loading with a new blister strip.

We claim:

1. A multiple-dose inhaler (10) for administering doses of medicament to a patient in very fine or micronized powder form, each of said doses being contained in an individual blister (30) in a blister sheet (60), the inhaler comprising means (18) for bringing the individual blisters (30) of the blister sheet (60) one after another into a piercing position, means (62) for piercing the individual blister (30) when in the piercing position, a delivery channel (82) through which the patient exerts an inhalation action, and an air intake (28) which communicates with said delivery channel when a blister has been pierced, a released dose of medicament being removable by an air stream generated by the inhalation action, said blister sheet (60) being in the form of a strip with the blisters (30) aligned, a connection channel (22) of rectilinear axis is provided coaxial with said delivery channel (82), said connection channel (22) connecting said delivery channel (82) to said air intake (28), the individual blister (30) when in its piercing position being arranged between said delivery channel (82) and said connection channel (22), within said connection channel (22) in proximity to an end (40) thereof adjacent to the blister when in its piercing position there being provided a cup (46) coaxial with said connection channel (22), the concavity of said cup facing said blister, said cup (46) having smaller dimensions than the dimensions of said connection channel (22) at the position occupied by said cup.

2. An inhaler as claimed in claim 1, wherein said cup (46) has a capacity substantially greater than the volume of the dose of medicament in powder form contained in the blisters (30).

3. An inhaler as claimed in claim 1, wherein said means for bringing the blisters in succession into the piercing position consist of a hollow drum (18) rotatable about its axis to carry the blisters (30), one after another, into the piercing position, the lateral surface of said drum (18) having equidistant seats (20) communicating with the interior of said drum (18) and arranged to receive the blisters (30) of said blister sheet (60), said blister sheet (60) being inserted into the inhaler (10) and wrapped at least through a certain portion about said drum (18), said connection channel (22) being arranged within said drum (18), said end (40) of said connection channel (22), towards which the concavity of said cup (46) faces, being arranged in a position corresponding with the piercing position.

4. An inhaler as claimed in claim 3, wherein said blister piercing means consist of a plunger or point (62) arranged coaxially within the mouthpiece (54) and axially movable in both directions.

5. An inhaler as claimed in claim 4, wherein said plunger or point (62) is rigid with said delivery channel (82), said plunger or point (62) being axially movable in both directions to pierce the blister (30) lying in the piercing position.

6. An inhaler as claimed in claim 1, wherein a vortex generating means (78) is provided in said delivery channel (82).

7. An inhaler as claimed in claim 6, wherein said vortex generating means consists of a fixed helix coaxial with said delivery channel (82) and carried by a coaxial shaft.

8. An inhaler as claimed in claim 1, wherein said blister sheet (60) comprises in one or both edges a series of equidistant notches (68) to be engaged by corresponding drive teeth (70) provided on said drum (18).

9. An inhaler as claimed in claim 1, wherein that blister of said blister sheet (60) which is the first to be inserted into the inhaler is a false blister (30') which projects to a lesser extent than the other blisters (30).

* * * * *